(12) United States Patent
Privat De Fortune et al.

(10) Patent No.: US 8,470,033 B2
(45) Date of Patent: Jun. 25, 2013

(54) FLEXIBLE INTRAOCULAR IMPLANT WITH CIRCULAR HAPTIC

(75) Inventors: Matthieu Privat De Fortune, Grenoble (FR); Yannick Joron, Argonnay (FR); Denis Gantin, Ayze (FR)

(73) Assignee: Philippe Sourdille, Liniers (FR)

( * ) Notice: Subject to any disclaimer, the term of this patent is extended or adjusted under 35 U.S.C. 154(b) by 255 days.

(21) Appl. No.: 12/668,842

(22) PCT Filed: Jul. 10, 2008

(86) PCT No.: PCT/FR2008/051301
§ 371 (c)(1),
(2), (4) Date: Jun. 21, 2010

(87) PCT Pub. No.: WO2009/013421
PCT Pub. Date: Jan. 29, 2009

(65) Prior Publication Data
US 2010/0286772 A1 Nov. 11, 2010

(30) Foreign Application Priority Data

Jul. 13, 2007 (FR) ...................... 07 56474

(51) Int. Cl.
*A61F 2/16* (2006.01)
(52) U.S. Cl.
USPC ........................... 623/6.42; 623/6.4; 623/6.49
(58) Field of Classification Search
USPC ................. 623/6.37, 6.4–6.46, 6.49
See application file for complete search history.

(56) References Cited

U.S. PATENT DOCUMENTS

| | | | |
|---|---|---|---|
| 6,409,762 B1 * | 6/2002 | Pynson et al. | 623/6.39 |
| 6,749,633 B1 * | 6/2004 | Lorenzo et al. | 623/6.36 |
| 2006/0161252 A1 * | 7/2006 | Brady et al. | 623/6.37 |

FOREIGN PATENT DOCUMENTS

| | | |
|---|---|---|
| DE | 37 22 910 A1 | 1/1989 |
| EP | 0 592 813 A | 4/1994 |
| FR | 2 786 686 A | 6/2000 |
| FR | 2 841 122 A | 12/2003 |
| WO | 2007/079315 A1 | 7/2007 |

OTHER PUBLICATIONS

English Translation of FR2786686, Publication date: Jun. 9, 2000, Inventor(s): Brauweiler, Peter, and Gantin Denis.*

* cited by examiner

*Primary Examiner* — David H Willse
*Assistant Examiner* — Tiffany Shipmon
(74) *Attorney, Agent, or Firm* — Kenyon & Kenyon LLP

(57) ABSTRACT

A flexible intraocular implant for placing in a capsular bag, the implant comprising an optical portion of substantially circular shape that presents an optical axis, and a haptic portion connected to the periphery of the optical portion, said haptic portion comprising:

a contact portion constituted by n (n≧2) contact elements in the form of circular arcs all having the same radius of curvature and each having an outer edge that is in contact with the equatorial zone of the capsular bag, and n connection elements, each connection element being connected via respective ends to two consecutive contact elements, presenting a deformable curved shape, and presenting stiffness that is much less than that of the contact elements; and n deformable connection arms each connected to the periphery of the optical portion and to a contact element.

11 Claims, 2 Drawing Sheets

FLEXIBLE INTRAOCULAR IMPLANT WITH CIRCULAR HAPTIC

CROSS-REFERENCE TO RELATED APPLICATIONS

This is a 371 national phase application of PCT/FR2008/051301 filed 10 Jul. 2008, claiming priority to French Patent Application No. FR 0756474 filed 13 Jul. 2007, the contents of which are incorporated herein by reference.

FIELD OF THE INVENTION

The present invention relates to a flexible intraocular implant with a circular haptic.

BACKGROUND OF THE INVENTION

As is well known, two types of material are suitable for use in making intraocular implants:
either rigid materials such as polymethyl methacrylate (PMMA);
or so-called "flexible" materials such as hydrophilic or hydrophobic acrylic materials, with an example thereof being known under the trademark Hydrogel.

The present invention relates to an implant made with the second type of material.

It is also known that intraocular implants are essentially constituted by two portions comprising firstly an optical portion constituting the system of the implant for correcting vision, and secondly a haptic portion that serves to hold the optical portion centered within the eye, and in the particular example described, within the capsular bag of the eye after the natural lens has been removed.

The haptic portion of the intraocular implant may have various shapes, and the main types of haptic are C-shaped or J-shaped loops, or indeed a circular shape that is connected to the optical portion by arms. The intraocular implant of the invention relates to a haptic portion that is of circular shape.

Once the intraocular implant has been placed in the eye, it must naturally perform the desired optical correction for the patient. This correction depends not only on the characteristics of the optical portion, but also on the position of the intraocular implant within the eye.

It is therefore important for the implant to retain the position within the eye that is initially established by the surgeon. Unfortunately, it is found that after an implant has been put into place in the capsular bag, the capsular bag tends to shrink in diameter over the period subsequent to putting the implant into place. This reduction in diameter may be by as much as 10%.

It will be understood that while the diameter of the capsular bag is reducing, when implants of conventional type are being used, there is a danger that the stresses applied by the capsular bag on the haptic portion as a result of its diameter shrinking will cause the optical portion to move axially along the direction of the optical axis of the eye. In addition, this reduction in diameter can give rise to stresses that lead to deformation of the haptic portion so that it is no longer circularly symmetrical, and that can cause the optical axis of the intraocular implant to be tilted relative to the optical axis of the patient's eye. Naturally, these two risks can give rise to very significant discomfort for the patient who has received the intraocular implant.

SUMMARY OF THE INVENTION

An object of the present invention is thus to provide an intraocular implant made of a flexible material and having a haptic portion of generally circular shape that deforms in such a manner that under the effect of the reduction in the diameter of the capsular bag, there is no significant movement of the optical portion in the direction of its optical axis nor is there any significant tilting of the optical axis of the implant relative to the optical axis of the eye.

According to the invention, in order to achieve this object, the flexible intraocular implant for placing in a capsular bag comprises an optical portion of substantially circular shape presenting an optical axis, and a haptic portion connected to the periphery of the optical portion, and it is characterized in that said haptic portion comprises:

a contact portion constituted by n ($n \geq 2$) contact elements in the form of circular arcs all having the same radius of curvature and each having an outer edge that is in contact with the equatorial zone of the capsular bag, and n connection elements, each connection element being connected via respective ends to two consecutive contact elements, presenting a deformable curved shape, and presenting stiffness that is much less than that of the contact elements; and n deformable connection arms, each having a first end connected to the periphery of the optical portion and a second end connected to a contact element, whereby under the effect of the diameter of the capsular bag diminishing, the connection elements and the connection arms deform without giving rise to significant movement of the optical portion in the direction of its optical axis, and without causing the optical axis of the implant to become significantly tilted relative to the optical axis of the patient's eye.

It will be understood that because of the difference in stiffness between the contact portions and the connection elements, it is the connection elements that deform under the effect of the stresses applied by the reduction in the diameter of the capsular bag, thereby reducing the outer diameter of the haptic portion of the implant as constituted by the contact elements. Under the effect of this reduction in diameter, the connection arms also deform. Thus, the optical portion of the intraocular implant is not subjected to significant movement in the direction of its optical axis, and given the circular symmetry of the haptic portion, the deformation is regular and circular and therefore does not lead to the optical axis of the optical portion becoming tilted relative to the optical axis of the eye.

Preferably, the intraocular implant is characterized in that the connection arms and the connection elements present a right section that is much smaller than the right section of the contact elements.

Also preferably, the intraocular implant is characterized in that each contact element has two faces, respectively a front face and a rear face, together with an outer face that is substantially parallel to the optical axis, the outer face co-operating with at least one of said two faces to form an angle of less than 120 degrees, thereby forming a square edge suitable for exerting large localized pressure on said capsular bag.

It can be understood that because of the presence of the sharp or square edge that exists on the contact elements of the haptic, these elements exert localized pressure on the capsular bag. This localized pressure serves to avoid proliferation of the pathogenic cells that often develop in the equatorial zone of the capsular bag and that tend to migrate towards the rear wall of the capsular bag. This avoids a secondary cataract appearing by said rear portion of the capsular bag being rendered opaque.

Also preferably, the contact elements and the connection elements together form a closed annular unit.

BRIEF DESCRIPTION OF THE DRAWINGS

A description of a preferred embodiment of the invention given by way of non-limiting example follows. The description refers to the accompanying figures, in which.

DETAILED DESCRIPTION

Figure 2:
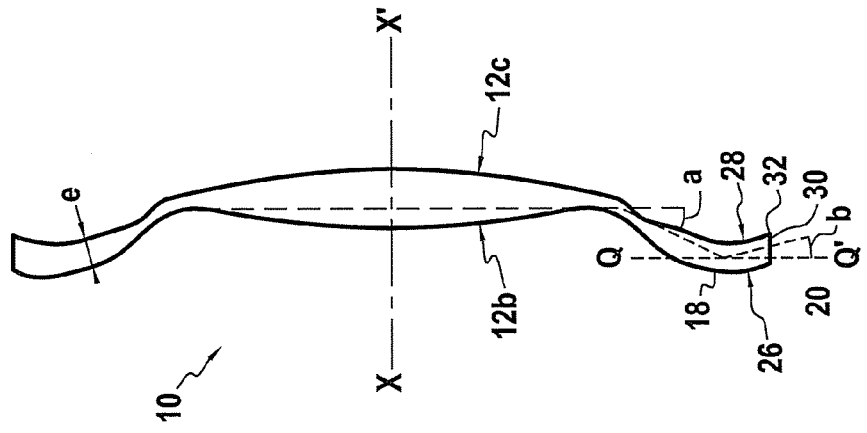
FIG. 2 is a side view of the intraocular implant.
Figure 1:
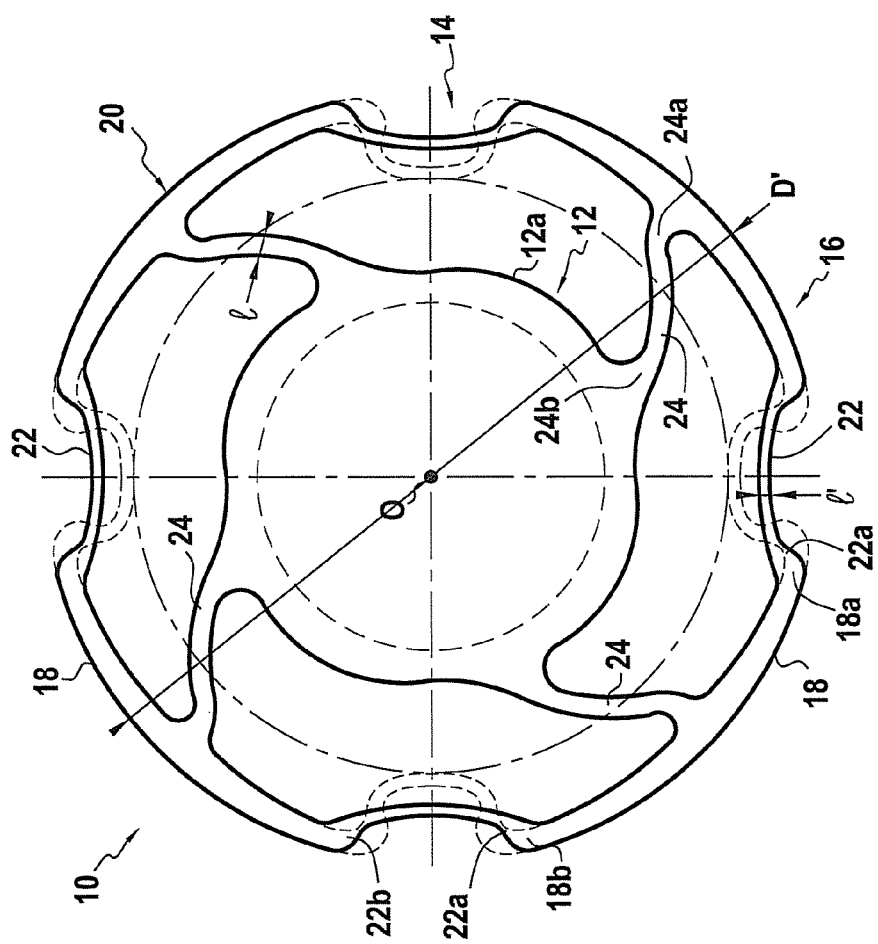
FIG. 1 is a front view of the intraocular implant at rest, i.e. without any stress applied to its haptic portion.

With reference initially to FIGS. 1 and 2, the main component elements of the intraocular implant 10 constituting a preferred embodiment of the invention are described.

The intraocular implant 10 is made from a so-called "flexible" material, typically a hydrophilic or hydrophobic acrylic, where one particular example is the product sold under the trademark Hydrogel. The implant is preferably made as a single piece.

The implant 10 is constituted by an optical portion 12 of generally circular shape presenting an edge 12a, a front refracting surface 12b, and a rear refracting surface 12c. The intraocular implant also has a haptic portion 14 constituted by an outer circular ring 16 constituted by n contact elements 18, each with an outer edge 20, and n connection elements 22 of curved shape, each interposed between two consecutive contact elements 18. In the example described, n is equal to 4, which corresponds to an optimum solution. Nevertheless, n could have some other value, and in any event it is not less than 2.

Preferably, all of the contact elements 18 correspond to the same length of circular arc. The same applies to the connection elements 22. By virtue of the connections that exist between the ends of the contact elements and the connection elements, these two types of element form a single, uninterrupted part, thereby constituting a closed and substantially-circular ring.

The ring 16 constituting the major fraction of the haptic portion is connected to the periphery 12a of the optical portion 12 by n arms 24. In the example described, there are four connection arms. At rest, each contact element 18 is in the form of a circular arc centered on the optical center of the optical portion 12, or more precisely on its optical axis X,X'. The ends 18a and 18b of each contact element 18 are connected to the ends 22a or 22b of an adjacent connection element 22. Each arm 24 has a first connection end 24a connected to a contact element 18 in its central portion and a second connection end 24b connected to the periphery of the optical portion 12, and these ends include fillets providing a certain amount of stiffening at both connections.

The contact elements 18 are of right section such that they are much stiffer than the connection elements 22, at least in a plane parallel to the optical plane of the optical portion 12 of the intraocular implant. Typically, the thickness e of the arms 24 (in the direction of the axis X,X') is much greater than the width l of these arms, being at least twice the width l. In the same manner, the width l' of each connection element 22 is much less than its thickness e'.

As can be seen more clearly in FIG. 2, the arms 24 slope forwards at an angle a, i.e. towards the front refracting surface 12b relative to the optical plane PP' of the optical portion 12. In contrast, the contact elements 18 slope backwards at an angle b relative to a plane QQ' parallel to the optical plane PP'.

Figure 4:
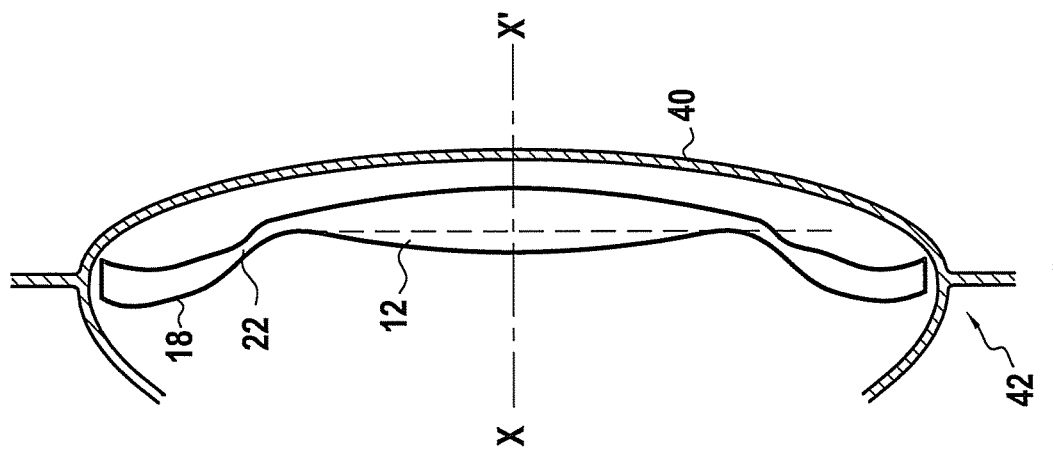
FIG. 4 is a simplified side view showing how the intraocular implant is placed in the capsular bag.
Figure 3:
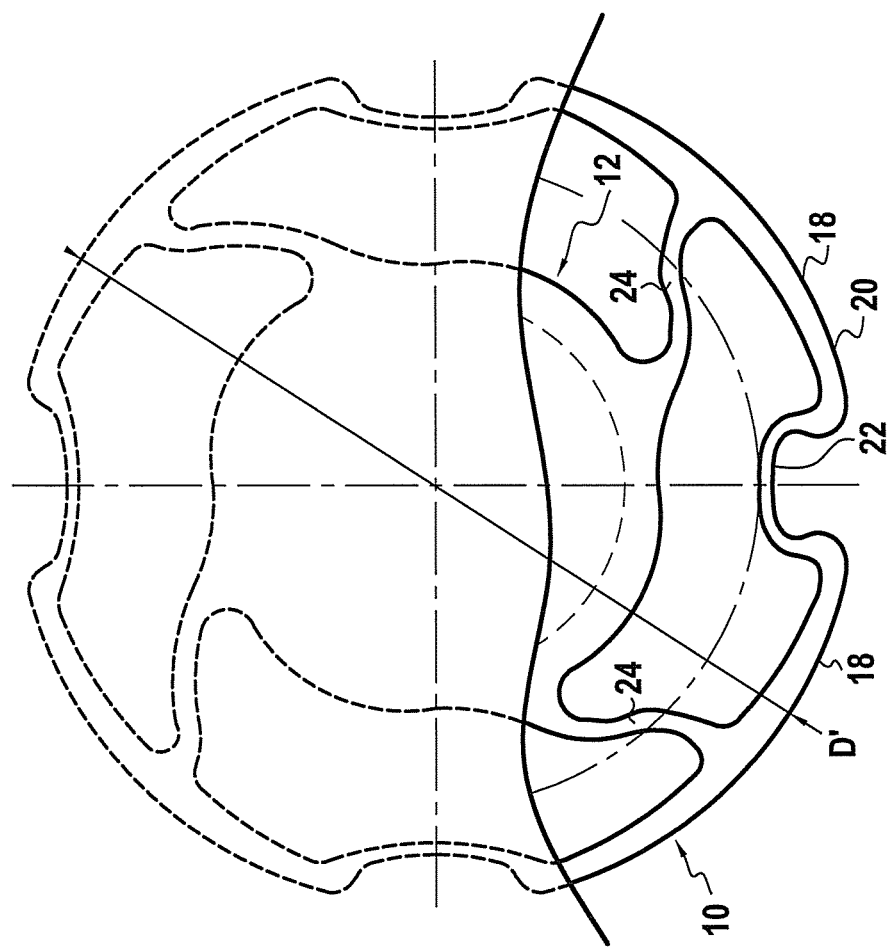
FIG. 3 is a fragmentary front view showing the haptic portion of the implant deformed.

The first angle a of the arms relative to the optical plane ensures that the rear refracting surface 12c of the optical portion 12 is held against the rear portion 40 of the capsular bag 42, as shown in FIG. 4. The angle b of the contact elements 18 serves to urge the optical portion forwards, thereby maintaining the optical portion 12 in stable manner against the rear wall 40 of the capsular bag, as described above.

As shown better in FIG. 2, each contact element 18 has a front face 26, a rear face 28, and an outer face 30. The rear faces 28 and the outer faces 30 are designed in such a manner as to constitute at least one square edge 32 suitable for exerting significant local pressure on the capsular bag in the equatorial region so as to form that which is commonly referred to as a "square edge" as mentioned above, the square edge being suitable for impeding proliferation of pathogenic cells from the equatorial zone of the capsular bag towards its rear wall 40.

The angle between the rear face 28 and the outer face 30 is less than 120 degrees in order to constitute the edge. In the example shown, this angle is less than 90 degrees because of the angle b of the contact elements 18.

As explained above, the connection elements 22 present stiffness in a plane parallel to the optical plane that is much less than the stiffness of the contact elements 18. Thus, under the effect of the above-mentioned contraction of the capsular bag that thus causes its diameter to be diminished, and because the contact elements and the connection elements together present the form of a closed ring, the stresses that result from this contraction applied to the outer edges of the contact elements 18 cause the connection elements 22 to bend without changing the shape of the contact elements 18 so that the outside diameter D' defined by the outer edges of the contact elements 18 becomes equal to the reduced diameter of the capsular bag. This deformation that is localized in the connection zones 22 avoids exerting rearward thrust on the optical portion 12 since the arms 24 also present a relatively large amount of flexibility in directions that are orthogonal to the optical axis XX' of the optical portion 12. The deformation of the arms 24 naturally follows the reduction in the outer diameter D' defined by the outer edges of the contact elements 18.

Since the diameter of the circle on which the outer edges 20 of the contact elements 18 lie is reduced simultaneously with the distance between the ends 24a and 24b of the arms 24 being diminished, there is substantially no movement.

In the particular example described, the outer diameter D of the intraocular implant at rest is equal to 10.5 millimeters (mm). The ring 16 can contract so as to obtain an outer diameter D' of the haptic when contracted that is about 8 mm, without significant movement of the optical portion 12 along the direction of the optical axis XX' of the implant. Furthermore, given the circular symmetry of the ring 16, the diameter reductions by localized deformation of the ring are regular. Consequently, this reduction in diameter gives rise to no significant tilting of the optical axis XX' of the optical portion 12 relative to the natural optical axis of the eye XX'.

Other embodiments may be envisaged providing the haptic portion is constituted essentially by a ring for contacting the equatorial zone of the capsular bag, said ring comprising substantially rigid portions in the form of circular arcs alternating with deformable connection zones that interconnect the ends of the rigid portions so that the reduction in the diameter of the ring takes place in localized manner in the flexible connection elements.

The invention claimed is:

1. A flexible intraocular implant for placing in a capsular bag, the implant comprising an optical portion of substantially circular shape that presents an optical axis, and a haptic portion connected to the periphery of the optical portion, wherein said haptic portion comprises:

a contact portion constituted by n (n≧2) contact elements in the form of circular arcs all having the same radius of curvature and each having an outer edge that is in contact with the equatorial zone of the capsular bag, and n connection elements, each connection element being connected via respective ends to two consecutive contact elements, presenting a deformable curved shape, and presenting stiffness that is much less than that of the contact elements; and n deformable connection arms, each having a first end connected to the periphery of the optical portion and a second end connected to a contact element, whereby under the effect of the diameter of the capsular bag diminishing, the connection elements and the connection arms deform without giving rise to significant movement of the optical portion in the direction of its optical axis, and without causing the optical axis of the implant to become significantly tilted relative to the optical axis of the eye.

2. An intraocular implant according to claim 1, wherein the connection arms and the connection elements present a cross section that is smaller than the cross section of the contact elements.

3. An intraocular implant according to claim 1, wherein the sum of the lengths of the contact elements is less than about 25 mm.

4. An intraocular implant according to claim 1, wherein each contact element has two faces, respectively, a front face and a rear face, together with an outer face that is substantially parallel to the optical axis, the outer face co-operating with at least one of said two faces to form an angle of less than 120 degrees, thereby forming a square edge suitable for exerting large localized pressure on said capsular bag.

5. An intraocular implant according to claim 1, wherein, at rest, the contact elements are ahead of the optical portion in the direction of the optical axis.

6. An intraocular implant according to claim 1, wherein, in projection onto a plane orthogonal to the optical axis, each connection arm slopes relative to a radius of the optical portion.

7. An intraocular implant according to claim 1, wherein the thickness of each connection arm in the direction of the optical axis is greater than its width in a direction orthogonal to the optical axis.

8. An intraocular implant according to claim 1, wherein the contact elements present an angle relative to the optical plane of the optical portion, each sloping towards the rear refracting surface.

9. An intraocular implant according to claim 1, wherein the contact elements and the connection elements together form a closed annular unit.

10. An intraocular implant according to claim 1, wherein the curved shape of each connection element has a substantially U shape, such that, a length between said respective ends connected to the two consecutive contact elements can be reduced by the diameter diminishing of the capsular bag.

11. An intraocular implant according to claim 1, wherein the haptic portion consists in a number of said contact elements, a number of said connection elements, and a number of said deformable arms, these three numbers being identical.

* * * * *

UNITED STATES PATENT AND TRADEMARK OFFICE
CERTIFICATE OF CORRECTION

PATENT NO. : 8,470,033 B2
APPLICATION NO. : 12/668842
DATED : June 25, 2013
INVENTOR(S) : Privat De Fortune et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 416 days.

Signed and Sealed this
Eighth Day of September, 2015

Michelle K. Lee
*Director of the United States Patent and Trademark Office*